(12) United States Patent
Harris et al.

(10) Patent No.: US 10,317,341 B2
(45) Date of Patent: Jun. 11, 2019

(54) MECHANICAL DEFORMATION SENSOR BASED ON PLASMONIC NANOPARTICLES

(71) Applicant: LytEn, Inc., Sunnyvale, CA (US)

(72) Inventors: Nadine Harris, Cambridge (GB);
Richard White, Cambridge (GB);
Michael Astley, Cambridge (GB)

(73) Assignee: LYTEN, INC., Sunnyvale, CA (US)

( * ) Notice: Subject to any disclaimer, the term of this patent is extended or adjusted under 35 U.S.C. 154(b) by 0 days.

(21) Appl. No.: 15/545,855

(22) PCT Filed: Jan. 28, 2016

(86) PCT No.: PCT/FI2016/050046
§ 371 (c)(1),
(2) Date: Jul. 24, 2017

(87) PCT Pub. No.: WO2016/124816
PCT Pub. Date: Aug. 11, 2016

(65) Prior Publication Data
US 2018/0017489 A1    Jan. 18, 2018

(30) Foreign Application Priority Data

Feb. 2, 2015 (EP) .................................. 15153474

(51) Int. Cl.
*G01N 21/552* (2014.01)
*G01N 21/65* (2006.01)
(Continued)

(52) U.S. Cl.
CPC ........... *G01N 21/554* (2013.01); *G01N 21/31* (2013.01); *G01N 21/3563* (2013.01);
(Continued)

(58) Field of Classification Search
CPC ........... G01N 21/554; G01N 33/54346; G01N 21/648; G01N 2021/5903;
(Continued)

(56) References Cited

U.S. PATENT DOCUMENTS 7,141,675 B2    11/2006 Tappan et al.
7,302,856 B2    12/2007 Tang et al.
(Continued)

FOREIGN PATENT DOCUMENTS

DE           4230087 A1    3/1994
JP        2012102221       5/2012
(Continued)

OTHER PUBLICATIONS

Schmucker et al., "Correction to Correlating Nanorod Structure with Experimentally Measured and Theoretically Predicted Surface Plasmon Resonance", ACS Nano, vol. 5, No. 9, Aug. 17, 2011, pp. 7685-7685.
(Continued)

*Primary Examiner* — Taeho Jo
(74) *Attorney, Agent, or Firm* — Dinsmore & Shohl LLP (57) ABSTRACT

An apparatus (517) comprising first and second plasmonic nanoparticles (502a, 502b) connected to one another by a deformable member (518), the first and second plasmonic nanoparticles each configured to exhibit a respective plasmon resonance when exposed to incident electromagnetic radiation (203), wherein, in a first configuration, the first and second plasmonic nanoparticles are in sufficient proximity to one another that their respective plasmon resonances can interact to produce a resulting plasmon resonance, and wherein mechanical deformation of the deformable member causes a variation in the relative position of the plasmonic nanoparticles to a second configuration to produce a detectable change in the resulting plasmon resonance of the first
(Continued)

configuration which can be used to determine said mechanical deformation.

20 Claims, 7 Drawing Sheets

(51) Int. Cl.
    *G01N 21/3563*     (2014.01)
    *G01N 21/41*     (2006.01)
    *G01N 21/3581*     (2014.01)
    *G01N 21/31*     (2006.01)

(52) U.S. Cl.
    CPC ....... *G01N 21/658* (2013.01); *G01N 21/3581* (2013.01); *G01N 21/4133* (2013.01)

(58) Field of Classification Search
    CPC ........... G01N 2021/7769; G01N 21/00; G01N 21/3563; G01N 21/3581; G01N 21/4133; G01N 21/645; G01N 21/31; G01N 21/658
    USPC ...................................................... 250/338.1
    See application file for complete search history.

(56) References Cited

U.S. PATENT DOCUMENTS

| | | | |
|---|---|---|---|
| 8,178,165 B2* | 5/2012 | Jin | B01J 35/0013 427/256 |
| 8,187,865 B2 | 5/2012 | Yun et al. | |
| 8,569,468 B2 | 10/2013 | Chen et al. | |
| 8,582,108 B2 | 11/2013 | Walters | |
| 9,595,328 B2* | 3/2017 | Loertscher | G11C 13/047 |
| 2002/0145792 A1* | 10/2002 | Jacobson | B41J 2/01 359/296 |
| 2003/0096113 A1* | 5/2003 | Jacobson | B41J 2/01 428/379 |
| 2007/0127164 A1* | 6/2007 | Ofek | B82Y 5/00 360/324 |
| 2008/0158542 A1 | 7/2008 | Otugen et al. | |
| 2008/0213130 A1* | 9/2008 | Pison | B82Y 5/00 422/68.1 |
| 2010/0053598 A1* | 3/2010 | Kwon | G01B 11/16 356/32 |
| 2010/0103504 A1* | 4/2010 | Lawandy | G02F 2/02 359/326 |
| 2010/0185121 A1 | 7/2010 | Carroll et al. | |
| 2011/0024698 A1* | 2/2011 | Worsley | B82Y 30/00 252/511 |
| 2011/0256577 A1* | 10/2011 | Himmelhaus | G01N 21/7746 435/29 |
| 2012/0105857 A1 | 5/2012 | Lee et al. | |
| 2012/0154793 A1 | 6/2012 | Pryce et al. | |
| 2012/0164433 A1* | 6/2012 | Advincula | B82Y 30/00 428/327 |
| 2012/0168506 A1* | 7/2012 | Ruehrmair | G06F 21/73 235/454 |
| 2012/0288960 A1 | 11/2012 | Minamiguchi et al. | |
| 2013/0045416 A1* | 2/2013 | Seferos | G01N 21/554 429/209 |
| 2013/0075699 A1* | 3/2013 | Brown | B82Y 30/00 257/21 |
| 2013/0108865 A1* | 5/2013 | Boulanger | B01D 67/0079 428/340 |
| 2013/0148194 A1* | 6/2013 | Altug | G01N 21/554 359/350 |
| 2013/0163001 A1 | 6/2013 | Tamura et al. | |
| 2014/0211195 A1 | 7/2014 | Barcelo et al. | |
| 2014/0249526 A1* | 9/2014 | Kotov | H01B 1/22 606/41 |
| 2015/0355040 A1* | 12/2015 | Sirbuly | G01L 1/242 356/73.1 |
| 2016/0083583 A1* | 3/2016 | Wilenski | C08J 5/10 523/222 |
| 2016/0146733 A1* | 5/2016 | Kim | B81C 1/0038 506/9 |
| 2016/0215104 A1* | 7/2016 | Farrugia | C09D 11/00 |
| 2016/0225449 A1* | 8/2016 | Loertscher | G11C 13/047 |

FOREIGN PATENT DOCUMENTS

| | | |
|---|---|---|
| WO | 2014/116758 A1 | 7/2014 |
| WO | 2014184530 | 11/2014 |

OTHER PUBLICATIONS

Willets et al., "Localized Surface Plasmon Resonance Spectroscopy and Sensing", Annual Review of Physical , Chemistry, vol. 58, May 5, 2007, pp. 267-297.
Teperik et al., "Robust Subnanometric Plasmon Ruler by Rescaling of the Nonlocal Optical Response", Physical Review Letters, vol. 110, No. 26, Jun. 28, 2013, pp. 263901-1-263901-5.
Bourlinos et al., "Synthesis, Characterization and Gas Sorption Properties of a Molecularly-Derived Graphite Oxide-Like Foam", Carbon, vol. 45, No. 4, Apr., 2007, pp. 852-857.
Vinod et al., "Low-Density Three-Dimensional Foam Using Self-Reinforced Hybrid Two-Dimensional Atomic Layers", Nature Communications, Jul. 29, 2014, pp. 1-9.
Jasuja et al., "Reversibly Compressible and Stretchable "Spring-like" Polymeric Nanojunctions Between Metal Nanoparticles", Small, vol. 4, No. 12, Dec. 2008, pp. 2181-2186.
Srivastava et al., "Super-Compressible DNA Nanoparticle Lattices", Soft Matter, No. 44, Aug. 12, 2013, pp. 10452-10457.
Bagheri et al., "Plasmons in Spatially Separated Double-Layer Graphene Nanoribbons", Journal of Applied Physics, vol. 115, No. 17, May 2014, pp. 174301-1-174301-8.
Slaughter et al., "Effects of Symmetry Breaking and Conductive Contact on the Plasmon Coupling in Gold Nanorod Dimers", ACS Nano, vol. 4, No. 8, Jul. 8, 2010, pp. 4657-4666.
Extended European Search Report received for corresponding European Patent Application No. 15153474.0, dated Aug. 26, 2015, 14 pages.
International Search Report and Written Opinion received for corresponding Patent Cooperation Treaty Application No. PCT/FI2016/050046, dated May 19, 2016, 18 pages.
Millyard Matthew G. et al. "Stretch-induced plasmonic anisotrophy of self-assembled gold nanoparticle mats", Applied Physics Letters, American Institute of Physics, US, vol. 100, No. 7, Feb. 13, 2012 pp. 73101.
Cole Robin et al. "Stertchable metal-elastomer nonovoids for tunable plasmons", Applied Physics Letters, American Institute of Physics, US, vol. 95, No. 1514 Oct. 2009, pp. 154103.
Venkata Ananth Tamma et al. "Turnale resonance in flexible plasmonic nanonstructures", Lasers and Electro-optics (CLEO), 2012 Conference on IEEE May 6, 2012, pp. 1-2.

* cited by examiner

1127 — Connect first and second plasmonic nanoparticles to one another by deformable member

Figure 12

1228 — Determine mechanical deformation of deformable member based on detected change in resulting plasmon resonance caused by mechanical deformation

MECHANICAL DEFORMATION SENSOR BASED ON PLASMONIC NANOPARTICLES

RELATED APPLICATION

This application was originally filed as PCT Application No. PCT/FI2016/050046 filed Jan. 28, 2016 which claims priority benefit from EP Application No 15153474.0 filed Feb. 2, 2015.

TECHNICAL FIELD

The present disclosure relates to the field of mechanical deformation sensors, associated methods and apparatus, and specifically concerns an apparatus configured to determine mechanical deformation of a deformable member based on a detected change in plasmon resonance caused by said mechanical deformation. Certain examples can be particularly suitable for the detection of analyte species which cause an associated mechanical deformation of the deformable member.

Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs), smartwatches, smart eyewear and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Research is currently being done to develop new sensors with improved sensitivity.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising first and second plasmonic nanoparticles connected to one another by a deformable member, the first and second plasmonic nanoparticles each configured to exhibit a respective plasmon resonance when exposed to incident electromagnetic radiation, wherein, in a first configuration, the first and second plasmonic nanoparticles are in sufficient proximity to one another that their respective plasmon resonances can interact to produce a resulting plasmon resonance, and wherein mechanical deformation of the deformable member causes a variation in the relative position of the plasmonic nanoparticles to a second configuration to produce a detectable change in the resulting plasmon resonance of the first configuration which can be used to determine said mechanical deformation.

The mechanical deformation may result from different stimuli including one or more of thermal expansion/contraction and deformation caused by one or more of acceleration, magnetic fields and acoustic pressure.

The deformable member may be one or more of a stretchable and compressible member configured to allow the proximity of the first and second plasmonic nanoparticles to be increased or decreased between the first and second configurations by the mechanical deformation, respectively.

The deformable member may be a flexible member configured to allow the relative orientation of the first and second plasmonic nanoparticles to be varied between the first and second configurations by the mechanical deformation.

The deformable member may be configured to undergo expansion between the first and second configurations on absorption of an analyte species from the surrounding environment, and detection of the corresponding change in the resulting plasmon resonance may be used to determine said expansion and hence the presence of the analyte species.

The deformable member may comprise a substrate on which the first and second plasmonic nanoparticles are supported.

The deformable member may be interpositioned between the first and second plasmonic nanoparticles.

The first and second plasmonic nanoparticles may or may not be spaced apart from one another by a gap in the first configuration.

The first and second nanoparticles may be spaced apart from one another by no more than 1 nm, 5 nm, 10 nm, 15 nm or 20 nm in the first configuration.

The first and second plasmonic nanoparticles may each have a long axis and a short axis, and the long axis of the first plasmonic nanoparticle may be collinear with the long axis of the second plasmonic nanoparticle in the first configuration.

The incident electromagnetic radiation may be polarized along a predefined polarization axis, and the apparatus may be configured such that the long axes of the first and second plasmonic nanoparticles are aligned substantially parallel to the polarization axis of the incident electromagnetic radiation in the first configuration.

At least one of the size, shape and material of the first and second plasmonic nanoparticles may be configured such that that the first and second plasmonic nanoparticles exhibit their respective plasmon resonances when exposed to one or more of ultraviolet, visible and infrared radiation.

The apparatus may comprise one or more further plasmonic nanoparticles, and the first, second and further plasmonic nanoparticles may be arranged such that each plasmonic nanoparticle is connected to an adjacent plasmonic nanoparticle by a deformable member.

The deformable member connecting one pair of adjacent plasmonic nanoparticles may be different to the deformable member connecting another pair of adjacent plasmonic nanoparticles.

The deformable member connecting one pair of adjacent plasmonic nanoparticles may be the same as the deformable member connecting another pair of adjacent plasmonic nanoparticles.

The deformable member connecting one pair of adjacent plasmonic nanoparticles may comprise the same material as the deformable member connecting another pair of adjacent plasmonic nanoparticles.

The deformable member may comprise a reversibly deformable material.

The deformable member may comprise one or more of a foam, a cross-linked polymer, a DNA lattice, an elastomer and a block copolymer.

The first and second plasmonic nanoparticles may have one or more of the same size, shape and material as one another.

The first and second plasmonic nanoparticles may comprise one or more of nanorods, nanowires and nanotubes.

The first and second plasmonic nanoparticles may comprise one or more of a noble metal, gold, platinum, silver and aluminium.

The mechanical deformation may comprise one or more of tensile, compressive, bending and shearing strain.

The apparatus may be one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, a sensor, a mechanical deformation sensor, and a module for one or more of the same.

According to a further aspect, there is provided a method of forming an apparatus, the method comprising:
  connecting first and second plasmonic nanoparticles to one another by a deformable member, the first and second plasmonic nanoparticles each configured to exhibit a respective plasmon resonance when exposed to incident electromagnetic radiation,
  wherein, in a first configuration, the first and second plasmonic nanoparticles are in sufficient proximity to one another that their respective plasmon resonances can interact to produce a resulting plasmon resonance, and
  wherein mechanical deformation of the deformable member causes a variation in the relative position of the plasmonic nanoparticles to a second configuration to produce a detectable change in the resulting plasmon resonance of the first configuration which can be used to determine said mechanical deformation.

According to a further aspect, there is provided a method of using an apparatus,
  the apparatus comprising first and second plasmonic nanoparticles connected to one another by a deformable member, the first and second plasmonic nanoparticles each configured to exhibit a respective plasmon resonance when exposed to incident electromagnetic radiation, wherein, in a first configuration, the first and second plasmonic nanoparticles are in sufficient proximity to one another that their respective plasmon resonances can interact to produce a resulting plasmon resonance, and wherein mechanical deformation of the deformable member causes a variation in the relative position of the plasmonic nanoparticles to a second configuration to produce a detectable change in the resulting plasmon resonance of the first configuration which can be used to determine said mechanical deformation,
  the method comprising:
    determining mechanical deformation of the deformable member based on a detected change in the resulting plasmon resonance caused by said mechanical deformation.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

Figure 1:
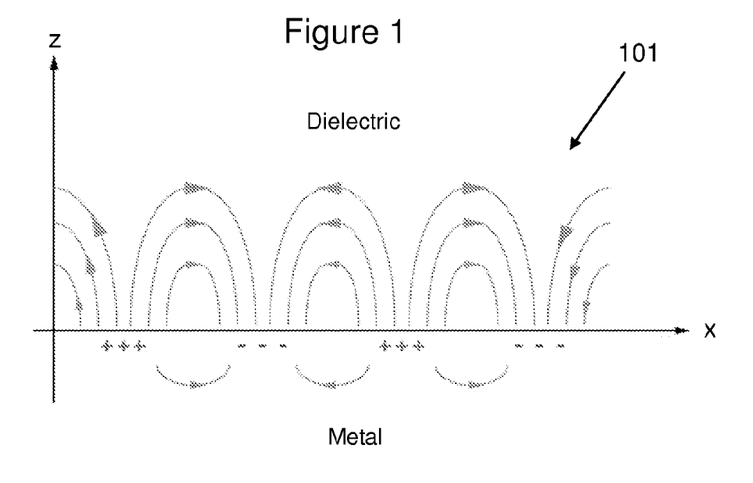
FIG. 1 illustrates schematically a surface plasmon polariton.

FIG. 1 illustrates schematically a surface plasmon polariton 101. Surface plasmons are coherent delocalised electron oscillations which are generated at a metal/dielectric interface in response to excitation by incident electromagnetic radiation. The charge motion in a surface plasmon also creates electromagnetic fields which extend outside the metal. A surface plasmon polariton 101 is therefore the total excitation including both the charge motion and the associated electromagnetic field. This phenomenon forms the basis of several existing techniques for measuring adsorption of material onto metallic surfaces.

Figure 2:
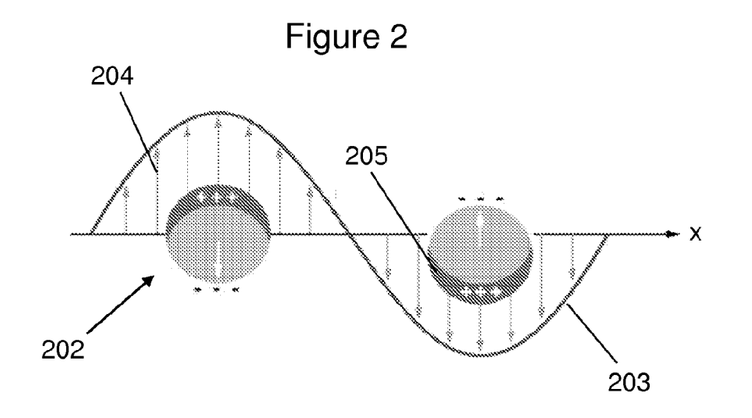
FIG. 2 illustrates schematically a localised surface plasmon.

FIG. 2 illustrates schematically a localised surface plasmon. Localised surface plasmons are change density oscillations confined to metallic nanoparticles 202. The illustrated example shows a plasmon oscillation on the surface of a metal sphere 202 in response to the electric field 204 of an incident electromagnetic wave 203. The displacement of the conduction electron charge cloud 205 is shown.

Excitation of localised surface plasmons by electromagnetic radiation results in strong light scattering, the appearance of intense surface plasmon absorption bands and an enhancement of the local electromagnetic fields. A localised surface plasmon resonance (referred to herein simply as a "plasmon resonance") is generated when the wavelength of the incident light on the nanoparticle is in resonance with an eigenmode of the nanoparticle plasmon oscillation. From Mie scattering theory, the resonance condition for the extinction cross-section for an incident plane wave on a metal nanoparticle is satisfied when, $$\Re_{[\varepsilon_{metal}(\lambda)]+\chi\varepsilon_{diel}}=0 \quad \text{(Equation 1)}$$

where $\varepsilon_{metal}$ and $\varepsilon_{diel}$ are the dielectric constants of the metal and dielectric material, respectively, and $\chi$ is a factor which is dependent on the geometry of the nanoparticle. The value of $\chi$ is 2 for a sphere, but may be as large as 20 for particle geometries with high aspect ratios (such as nanorods). Based on this equation, materials which possess a negative real and small positive imaginary dielectric constant are capable of supporting surface plasmons (such as silver and gold). Conditions for excitation are only satisfied, however, if the real dielectric constant of the metal is greater in magnitude than the real dielectric constant of the dielectric material.

The extinction spectrum (absorption plus scattering) of a metal sphere is given as:

$$E(\lambda) = \frac{24\pi^2 Na^3 \varepsilon_{out}^{3/2}}{\lambda \ln(10)} \left[ \frac{\varepsilon_i(\lambda)}{(\varepsilon_r(\lambda) + \chi\varepsilon_{out})^2} \right] \quad \text{(Equation 2)}$$

where $\varepsilon_{in}$ and $\varepsilon_{out}$ are the dielectric constants of the metal nanoparticle and external environment, respectively, $\varepsilon_r$ and $\varepsilon_i$ are the real and imaginary components of the wavelength-dependent metal dielectric function, respectively, Na is Avagadro's constant, and $\lambda$ is the wavelength of the incident radiation. The extinction of light associated with the nanoparticle is dependent on any changes in $\varepsilon_{out}$ (or refractive index, n, since both are related by $\varepsilon=n^2$).

Equations 1 and 2 show that the extinction spectrum is dependent on the local dielectric environment ($\varepsilon_{diel}$ and $\varepsilon_{out}$ in equations 1 and 2, respectively). Therefore, any changes in the local dielectric environment will cause a shift in the extinction wavelength maximum (resonance wavelength), $\lambda_{max}$, and a change in intensity. This can be used to detect the presence and/or concentration of analyte species on the surface of the nanoparticle or in the surrounding dielectric medium.

Figure 3:
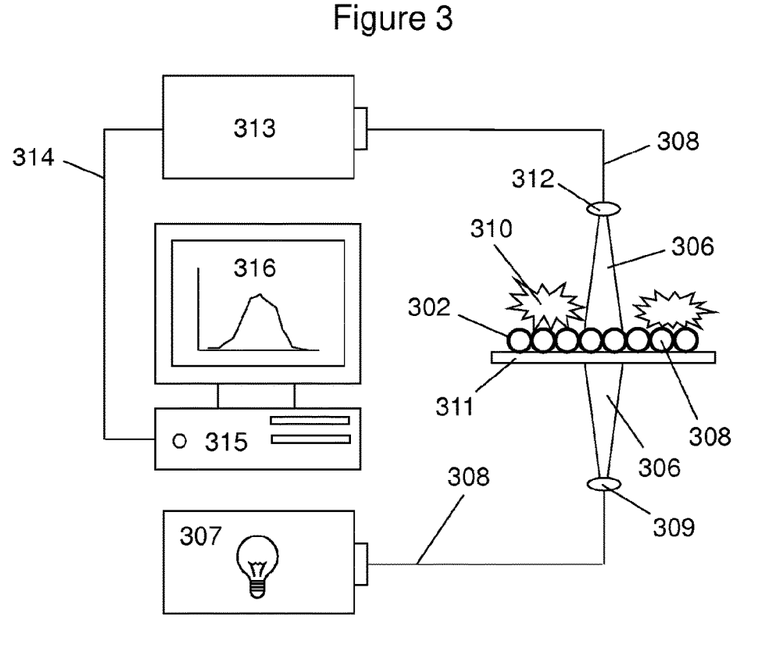
FIG. 3 illustrates schematically a typical experimental setup for measuring extinction spectra of nanoparticles.

FIG. 3 shows one approach to the measurement of nanoparticle plasmon resonance spectra—transmission surface plasmon resonance spectroscopy. Here, one measures the extinction spectrum of the nanoparticles by recording the wavelength dependence of light passing through the sample. In this example, light 306 from a source 307 is directed along an optical fibre 308 and focused by a lens 309 onto the specimen. The specimen is immersed in a dielectric medium (such as air, water or another solvent) and comprises a layer of nanoparticles 302 which are bound to analyte molecules 310 and supported on a transparent substrate 311. When a plasmon resonance is excited, the wavelengths of light causing the excitation are absorbed and/or scattered. The beam of illumination 306 is detected behind the specimen using the probe 312 of a spectrophotometer 313. Light incident on the probe is then directed to a charge-coupled device (CCD) camera (not shown) inside the spectrophotometer. The data is subsequently sent (via electrical cables 314, for example) to a computer 315 for processing, and an extinction spectrum 316 is displayed for analysis.

Figure 4:
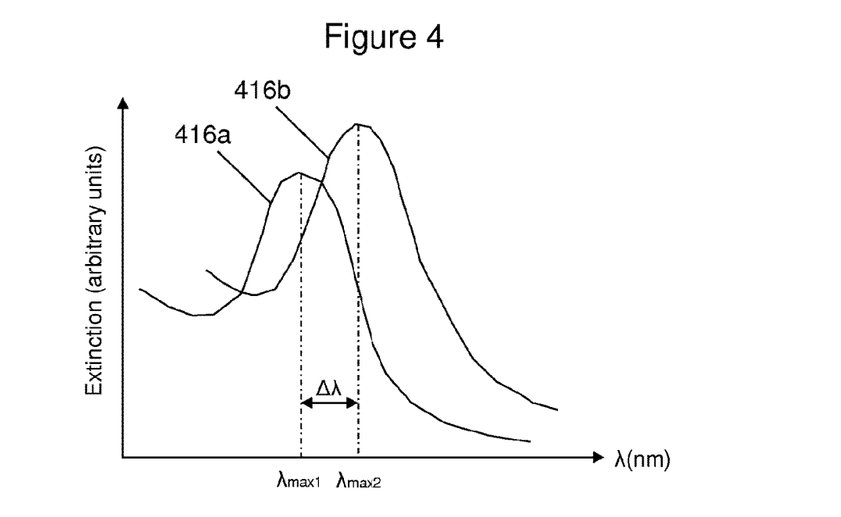
FIG. 4 illustrates schematically a typical extinction spectrum.

FIG. 4 shows an example of a typical extinction spectrum which reveals the absorption and/or scattering of each wavelength of light. The transmission geometry yields the plasmon resonance wavelength as a maximum value in the extinction curve. The peaks from before and after the analytes are bound to the nanoparticles are denoted by numerals 416a and 416b, respectively, and the corresponding plasmon resonance wavelengths as $\lambda_{max1}$ and $\lambda_{max2}$. In this case, binding at the surface of the nanoparticles has resulted in a shift in peak wavelength, $\Delta\lambda$, as well as an increase in intensity.

Rather than using surface plasmon resonance spectroscopy to directly detect analyte species, the present application applies the technique to the detection/measurement of mechanical deformation (which can, in certain embodiments, be used to detect analyte species indirectly). Existing deformation sensors typically convert the mechanical deformation of a material into an electrical signal, and are usually limited to the detection of a single type of strain. The use of surface plasmon resonance spectroscopy, however, allows several different types of strain to be determined from an optical signal. This removes the need for electrical contacts, which is particularly advantageous for biomedical applications where the attachment of contacts can be difficult. It also provides a highly sensitive system in which even nanoscale displacements of material can produce a detectable signal.

Figure 5:
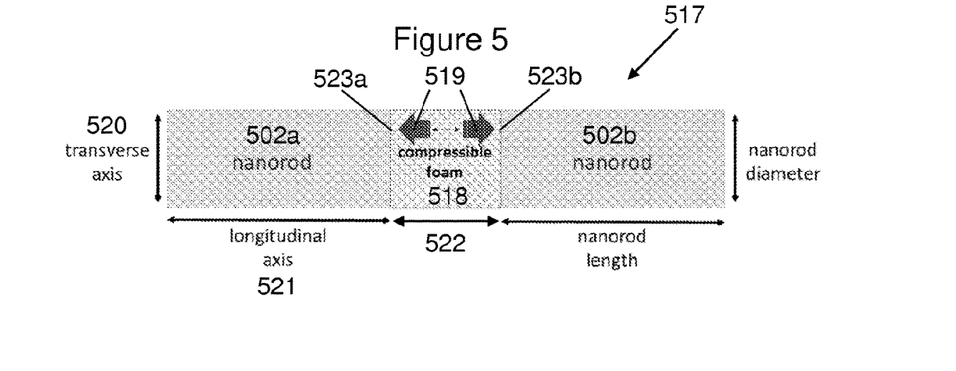
FIG. 5 illustrates schematically one example of the present apparatus.

FIG. 5 shows one example of the present apparatus 517. The apparatus comprises first 502a and second 502b plasmonic nanoparticles connected to one another by a deformable member 518 (which may or may not be reversibly deformable). The term "plasmonic" in this sense can be taken to mean that the first 502a and second 502b nanoparticles are each configured to exhibit a respective plasmon resonance when exposed to incident electromagnetic radiation.

The apparatus 517 is deformable between first and second configurations. In the first configuration (as shown in FIG. 5), the first 502a and second 502b plasmonic nanoparticles are in sufficient proximity to one another that their respective plasmon resonances can interact to produce a resulting (e.g. combined/cumulative) plasmon resonance. If a stress is then applied to the apparatus 517, mechanical deformation 519 of the deformable member 518 to the second configuration causes a variation in the relative position of the plasmonic nanoparticles 502a,b to produce a detectable change in the resulting plasmon resonance of the first configuration which can be used to determine said mechanical deformation 519.

In this particular example, the first 502a and second 502b plasmonic nanoparticles are nanorods. When an individual nanorod 502a is illuminated by electromagnetic radiation, it produces two main plasmonic resonances (amongst others): one which corresponds to excitation along the short/transverse axis 520 (transverse resonance), and another which corresponds to excitation along the long/longitudinal axis 521 (dipole resonance). The size and position of these resonances within the extinction spectrum depends on the size, shape and material of the nanorod 502a.

If another nanorod 502b is then arranged collinearly at the end of the first rod 502a so that there is a small gap 522 (e.g. 1-20 nm) between the respective end faces 523a,b, this will cause the dipole resonance of each rod 502a,b to interact and red-shift the resonance from its original position to produce the resulting (e.g. combined/cumulative) plasmon resonance. The shift-variation of the plasmon resonance depends on the gap size 522. In general, the closer the rod end faces 523a,b, the greater the red-shift. Therefore, if the nanorods 502a,b have a pre-calibrated proximity which gives rise to an initial resulting plasmon resonance, a change in their proximity will produce a change in the resulting plasmon resonance from which the new proximity (and/or change in proximity) can be determined.

Simulations were performed to demonstrate this technique in which the gap between two collinear gold nanorods was increased from 5 nm to 30 nm whilst the nanorods were illuminated by electromagnetic radiation in the low infrared range. In these simulations, one of the nanorods had a length of 260 nm and a diameter of 60 nm, the other nanorod had a length of 125 nm and a diameter of 60 nm, and the nanorods were immersed in (and therefore separated by) water.

Figure 6:
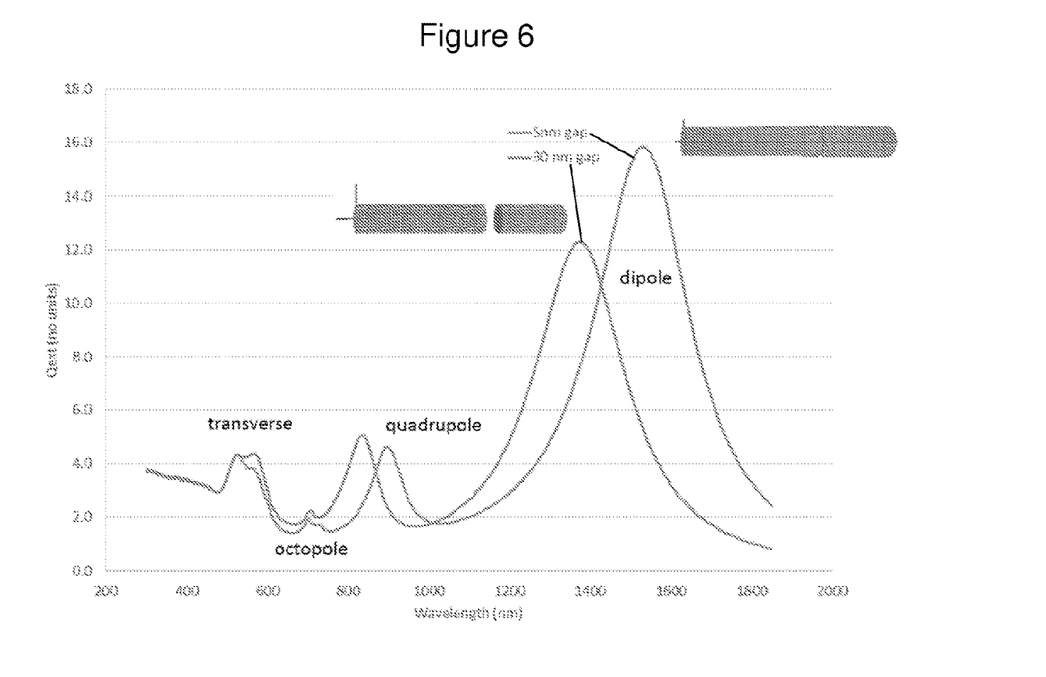
FIG. 6 illustrates schematically a change in the extinction spectrum caused by a variation in the nanoparticle spacing.

FIG. 6 shows the simulated extinction spectra. As can be seen from these graphs, the wavelength of the resulting dipole resonance shifted from 1530 nm to 1370 nm as the interparticle spacing increased from 5 nm to 30 nm. In addition, the quadrupole resonance shifted from 900 nm to 840 nm. As mentioned above, this measured shift in resonance wavelength allows a quantitative measurement of the nanoparticle displacement.

The present technique is not limited to gold nanorods. In general, any size, shape and material which exhibits the above-mentioned behaviour is suitable for use. In this respect, the first and second plasmonic nanoparticles may comprise nanorods, nanowires or nanotubes formed from one or more of metal, gold, platinum, silver, aluminium or another noble metal. There is also no need for the first and second plasmonic nanoparticles to be identical. Therefore, the first plasmonic nanoparticle may or may not have one or more of the same size, shape and material as the second plasmonic nanoparticle. Furthermore, shifts in quadrupole or other higher order resonances rather than dipole resonance may be used to measure/detect mechanical deformation (shifts in transverse resonance peak positions may be considered small with respect to shifts in other resonances, for a given diameter nanorod, and also the transverse resonance can be considered to be largely dependent upon the nanorod diameter, rather than the interparticle spacing).

Furthermore, although electromagnetic radiation in the low infrared range was used in the simulations of FIG. 6, at least one of the size, shape, material and spacing of the first and second nanoparticles may be configured such that they exhibit their respective plasmon resonances when exposed to one or more of ultraviolet, visible and infrared radiation. For example, a deep infrared sensor could be configured by reducing the interparticle spacing or increasing the aspect ratio of the gold nanorods. Similarly, a visible sensor could be configured by reducing the aspect ratio of the gold nanorods or replacing them with silver nanorods, whilst an ultraviolet sensor could be configured by replacing the gold nanorods with aluminium nanorods.

The configuration of the deformable member may also depend on the particular application. In the example shown in FIG. 5, the deformable member 518 is one or more of a stretchable and compressible member configured to allow the proximity of the first 502a and second 502b plasmonic nanoparticles to be increased or decreased between the first and second configurations by the mechanical deformation 519, respectively. This allows the apparatus 517 to be used for detecting/measuring tensile and compressive strain. Additionally or alternatively, the deformable member 518 may be configured to allow the relative orientation of the first 502a and second 502b plasmonic nanoparticles to be varied between the first and second configurations by the mechanical deformation 519. Such a configuration allows the apparatus 517 to be used for detecting/measuring bending or shearing strain.

Figure 7:
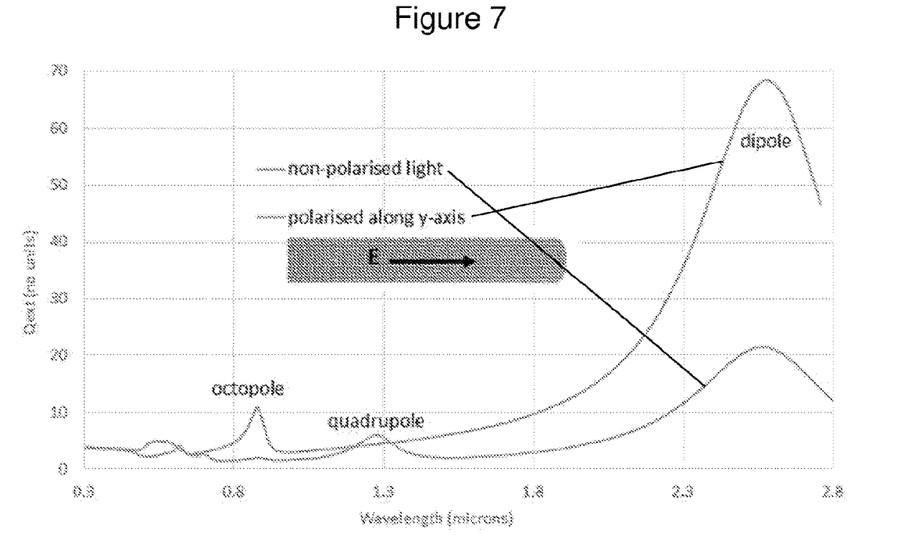
FIG. 7 illustrates schematically a change in the extinction spectrum caused by a variation in the nanoparticle orientation.

FIG. 7 demonstrates how a variation in the nanoparticle orientation can also cause a change in the extinction spectrum. This figure shows a simulated extinction spectrum obtained by exposing a single nanorod to polarised and non-polarised light. In these simulations, a gold nanorod of 640 nm in length and 80 nm in diameter was used, and the polarisation of the light was oriented parallel to the long axis of the nanorod.

As can be seen from the graphs, only odd order resonances (in this case dipole and octopole) were excited when the electric field of the incident light was oriented along the long axis of the rod, whilst all resonances (dipole, quadrupole, octopole and transverse) were excited by the non-polarised light. Furthermore, the quadrupole resonance was excited by the non-polarised light at the expense of the magnitude of the octopole resonance, which almost disappeared completely.

This sensitivity to polarisation enables the present apparatus to be used to detect bending or shearing strain. For example, if the apparatus of FIG. 5 was illuminated by incident light polarised along the long axes 521 of the nanorods 502a,b, a change in the relative orientation of the rods 502a,b from this first configuration to a second configuration would cause a corresponding change in the extinction spectrum.

Figure 8:
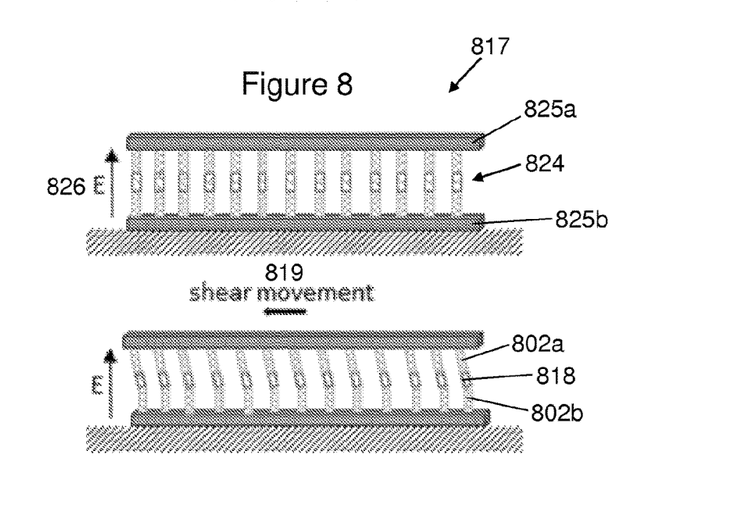
FIG. 8 illustrates schematically a variation in the relative orientation of the nanoparticles caused by a shearing stress.

FIG. 8 shows another example of the present apparatus 817. In this example, the apparatus 817 comprises a plurality of plasmonic nanorod pairs 824 each having a deformable member 818 interpositioned between first 802a and second 802b plasmonic nanorods. Within each pair 824, the long axis of the first nanorod 802a is collinear with the long axis of the second nanorod 802b, and the nanorod pairs 824 are held parallel to one another by supporting substrates 825a,b. As can be seen in this figure, a first supporting substrate 825a is attached to one end of each nanorod pair 824 (i.e. at an end face of the first nanorods 802a) and a second supporting substrate 825b is attached to the opposite end of each nanorod pair 824 (i.e. at an end face of the second nanorods 802b).

When a shearing force 819 is applied to the apparatus 817, the first supporting substrate 825a will move laterally relative to the second supporting substrate 825b causing a change in the relative orientation of the first 802a and second 802b nanorods of each nanorod pair 824 from the first (initial) configuration to a second configuration. As in the example above, this change in orientation will cause a corresponding variation in the extinction spectrum if the polarisation 826 of the incident electromagnetic radiation is oriented parallel to the long axes of the first 802a and second 802b nanorods in the first configuration. Detection of the quadrupole resonance, or decrease in the dipole resonance (for example), could then be used to determine that a shearing force 819 has been applied. Furthermore, if the magnitude of a particular resonance is calibrated for different shearing forces 819, it may be possible to quantify the applied force 819 based on a measurement of said resonance (or change in resonance).

Although the use of polarised light is described above for determining bending and shearing strains, non-polarised light could also be used. This is because a change in the relative orientation of the first and second nanorods will affect the interaction of their respective plasmon resonances due to the axial misalignment and change in proximity of their end faces.

Figure 9:
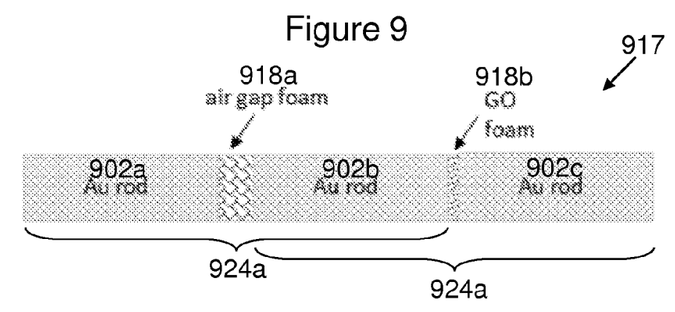
FIG. 9 illustrates schematically another example of the present apparatus.

FIG. 9 shows another example of the present apparatus 917. In this example, the apparatus 917 comprises a further plasmonic nanoparticle 902c in addition to the first 902a and second 902b plasmonic nanoparticles, the nanoparticles 902a-c arranged such that each plasmonic nanoparticle 902a-c is connected to an adjacent plasmonic nanoparticle 902a-c by a deformable member 918a,b. Although only one further nanoparticle 902c is shown here, the apparatus 917 may comprise a plurality of further nanoparticles 902c. Furthermore, other types of nanoparticle could be used instead of the nanorods illustrated here.

In some embodiments, the deformable member 918a connecting one pair 924a of adjacent plasmonic nanoparticles 902a,b may be the same deformable member 918b connecting another pair 924b of adjacent plasmonic nanoparticles 902b,c (e.g. the deformable members 918a,b may be made from the same material). This setup could be used to monitor mechanical deformation at different regions of a single apparatus 917 by illuminating a nanoparticle pair 924a,b within each region with electromagnetic radiation and measuring its respective plasmon resonance.

In other embodiments, the deformable member 918a connecting one pair 924a of adjacent plasmonic nanoparticles 902a,b may be different to the deformable member 918b connecting another pair of adjacent plasmonic nanoparticles 902b,c (e.g. the deformable members 918a,b may be made from different materials). Due to the different configurations of each deformable member 918a,b (e.g. stretchable, compressible and/or flexible), this setup could be used to monitor different types of deformation (e.g. tensile, compressive, bending and/or shearing strain) with a single apparatus 917 by illuminating the relevant nanoparticle pairs 924a,b with electromagnetic radiation and measuring their respective plasmon resonances.

In some cases, the deformable member may be configured to undergo expansion between the first and second configurations on absorption of an analyte species from the surrounding environment. In this scenario, detection of the corresponding change in the resulting plasmon resonance could be used to determine said expansion and hence the presence of the analyte species. For example, the hydrophilic nature of graphene oxide allows it to absorb water from the surrounding environment. Therefore, if a graphene oxide foam is used to connect a pair of adjacent plasmonic nanoparticles, the foam will expand on absorption of the water which may be used to provide an optical indication of the environmental humidity.

In the example shown in FIG. 9, the deformable member 918a separating the first 902a and second 902b nanorods comprises an air-gap compressible foam whilst the deformable member 918b separating the second 902b and third 902c nanorods comprises a graphene oxide foam. The first 902a and second 902b nanorods (together with the air-gap compressible foam 918a) could therefore be used to determine the presence and/or magnitude of a longitudinal tensile or compressive strain. In addition, the second 902b and third 902c nanorods (together with the graphene oxide foam 918b) could be used to determine the presence and/or amount of water in the surrounding environment. The use of different deformable members 918a,b within the same apparatus 917 therefore increases the sensing functionality.

In each of the examples described and illustrated thus far, the deformable member is interpositioned between the adjacent plasmonic nanoparticles. In some cases, however, the deformable member could comprise a substrate on which the adjacent plasmonic nanoparticles are supported. For example, the plasmonic nanoparticles could simply be grown or deposited (and fixed in position) on top of a planar substrate formed from the one or more desired deformable materials. This configuration may facilitate fabrication of the apparatus by avoiding the need to deposit a material between the nanoparticles, which could be challenging with high aspect ratio nanoparticles such as nanorods.

Figure 14A:
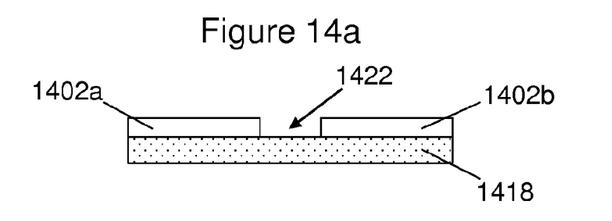
FIGS. 14a-c illustrate schematically further examples of the present apparatus.
Figure 14B:
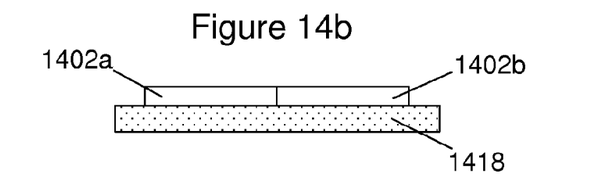
Figure 14C:
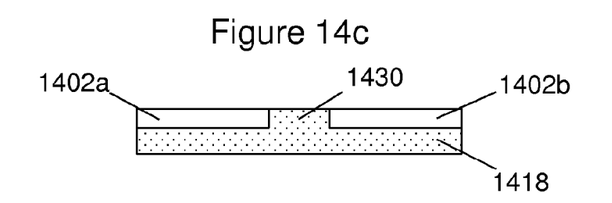

FIGS. 14a-c show examples of the present apparatus 1417 in which the deformable member 1418 comprises a supporting substrate. In FIG. 14a, the first 1402a and second 1402b plasmonic nanoparticles are formed on the upper surface of the supporting substrate 1418 such that a gap 1422 exists between the nanoparticles 1402a,b in the first configuration. In the example of FIG. 14b, on the other hand, the first 1402a and second 1402b plasmonic nanoparticles are positioned on the substrate 1418 such that there is substantially no gap 1422 between the nanoparticles 1402a,b in the first configuration. In the example of FIG. 14c, the substrate 1418 comprises a protrusion 1430 which separates the first 1402a and second 1402b plasmonic nanoparticles. In this latter scenario, therefore, the substrate 1418 supports, and is interpositioned between, the first 1402a and second 1402b plasmonic nanoparticles.

A number of different methods may be used to fabricate the present apparatus. One process involves the use of on-wire lithography to form a one-dimensional gapped nanorod structure via an aluminium anode oxide template. In this approach, the first nanorod is electroplated followed by the deposition of a deformable member and second nanorod, and the subsequent removal of the structure from the template. The first and second nanorods may comprise one or more of gold, platinum, silver, aluminium or another noble metal. A variety of different materials could be used to form the deformable member. Suitable examples include a foam (e.g. graphene foam, graphene oxide foam or a hybrid graphene oxide-boron nitride foam), a cross-linked polymer, a DNA lattice, an elastomer (polydimethylsiloxane), and a block copolymer.

Due to the dimensions of the plasmonic nanoparticles, any porous deformable member used to connect the nanoparticles should have pore sizes in the nanometer range. This can be achieved by removing one phase of a block copolymer to produce a gyroid structure, or by depositing the deformable material onto a nanoporous metal foam template using chemical vapour deposition (or another deposition technique).

Figure 10:
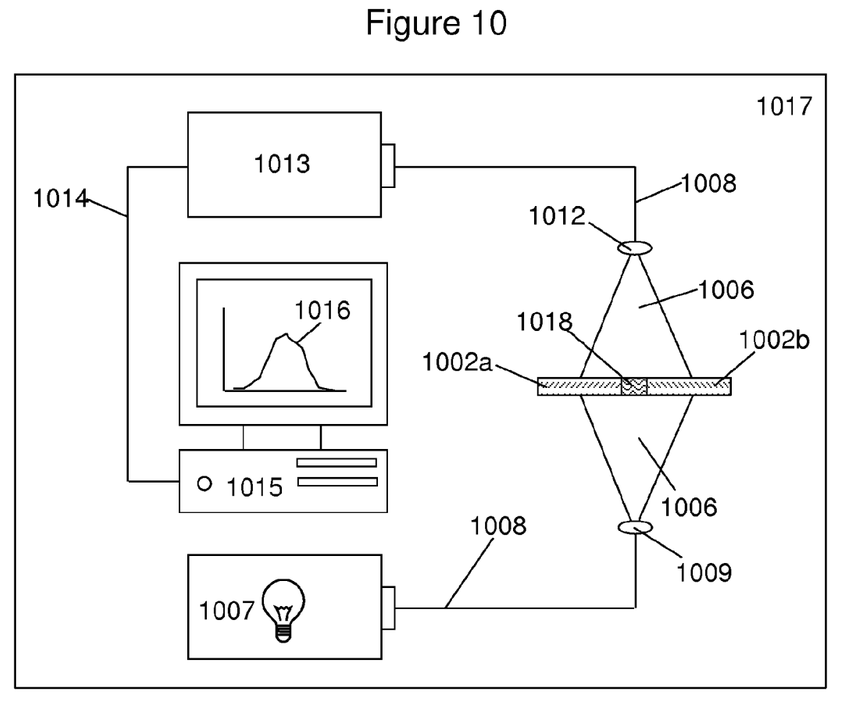
FIG. 10 illustrates schematically another example of the present apparatus.

FIG. 10 shows another example of the present apparatus 1017. The apparatus 1017 may be one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, a sensor, a mechanical deformation sensor, and a module for one or more of the same.

In this example, the apparatus 1017 comprises the plasmonic nanoparticles 1002a,b and deformable member(s) 1018 described previously, together with the spectroscopy equipment of FIG. 3. In particular, the spectroscopy equipment comprises a light source 1007 for generating the electromagnetic radiation 1006, a lens 1009 for focussing the electromagnetic radiation 1006 onto the plasmonic nanoparticles 1002a,b, a probe 1012 for detecting the electromagnetic radiation 1006 behind the specimen after absorption/scattering, optical fibres 1008 for directing the electromagnetic radiation 1006 to the lens 1009 and from the probe 1012, a spectrophotometer 1013 for measuring the absorption/scattering of the electromagnetic radiation 1006 by the plasmonic nanoparticles 1002a,b, an electrical cable 1014 for transferring the absorption/scattering data from the spectrophotometer 1013 to a computer 1015, and a computer 1015 for processing and displaying the absorption/scattering data as an extinction spectrum 1016.

The computer 1015 itself may be configured to measure the resulting/combined/cumulative plasmon resonance of the plasmonic nanoparticles 1002a,b and determine any change in the plasmon resonance, e.g. relative to an initial measurement in the first configuration. Additionally or alternatively, the computer 1015 may be configured to determine the mechanical deformation of the deformable member 1018 based on the detected change in plasmon resonance caused by said mechanical deformation.

To achieve this, the computer 1015 may comprise a storage medium (not shown) configured to store the absorption/scattering data from the spectrophotometer 1013 and a processor (not shown) configured to perform the above-mentioned calculations. The processor may also be configured for general operation of the computer 1015 by providing signalling to, and receiving signalling from, the other components to manage their operation. In addition, the storage medium may be configured to store computer code configured to perform, control or enable operation of the computer 1015. The storage medium may also be configured to store settings for the other components such that the processor can retrieve the settings to manage their operation.

The processor may be a microprocessor, including an Application Specific Integrated Circuit (ASIC). The storage medium may be a temporary storage medium such as a volatile random access memory. On the other hand, the storage medium may be a permanent storage medium such as a hard disk drive, a flash memory, or a non-volatile random access memory.

Figure 11:
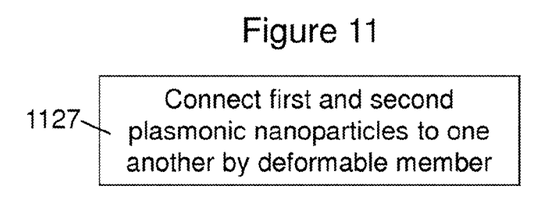
FIG. 11 illustrates schematically the main steps of a method of making the present apparatus.
Figure 12:
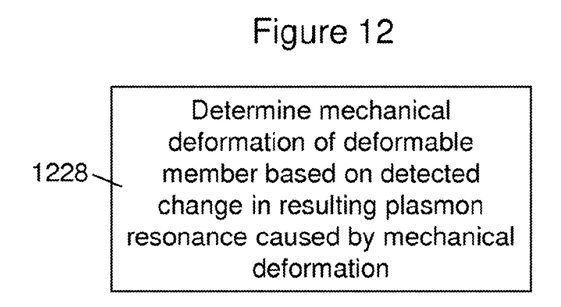
FIG. 12 illustrates schematically the main steps of a method of using the present apparatus.

The main steps of a method of forming an apparatus described herein are shown schematically in FIG. 11. This method generally comprises connecting 1127 first and second plasmonic nanoparticles to one another by a deformable member. Similarly, the main steps of a method of using an apparatus described herein are shown schematically in FIG. 12. This method generally comprises determining 1228 mechanical deformation of the deformable member based on a detected change in the resulting plasmon resonance caused by said mechanical deformation.

Figure 13:
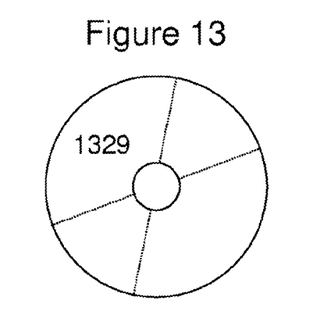
FIG. 13 illustrates schematically a computer-readable medium comprising a computer program configured to perform, control or enable the method steps of FIG. 11 or 12.

FIG. 13 illustrates schematically a computer/processor readable medium 1329 providing a computer program according to one embodiment. The computer program may comprise computer code configured to perform, control or enable the method steps 1127, 1228 of FIG. 11 and/or FIG. 12. In this example, the computer/processor readable medium 1329 is a disc such as a digital versatile disc (DVD) or a compact disc (CD). In other embodiments, the computer/processor readable medium 1329 may be any medium that has been programmed in such a way as to carry out an inventive function. The computer/processor readable medium 1329 may be a removable memory device such as a memory stick or memory card (SD, mini SD, micro SD or nano SD).

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising first plasmonic nanoparticles, second plasmonic nanoparticles, and one or more further plasmonic nanoparticles each configured to exhibit a respective plasmon resonance when exposed to incident electromagnetic radiation, the first, second and one or more further plasmonic nanoparticles arranged such that each plasmonic nanoparticle is connected to an adjacent plasmonic nanoparticle by a deformable member, the deformable member connecting one pair of adjacent plasmonic nanoparticles is formed of a different material relative to the deformable member connecting another pair of adjacent plasmonic nanoparticles such that each deformable member is configured to undergo a different type of mechanical deformation relative to an adjacent deformable member dependent on the material composition of each deformable member, respectively, wherein, in a first configuration, when two adjacent nanoparticles are in sufficient proximity to one another their respective plasmon resonances can interact to produce a resulting plasmon resonance, and wherein mechanical deformation of the deformable member causes a variation in the relative position of the respective adjacent plasmonic nanoparticles to a second configuration to produce a detectable change in the resulting plasmon resonance of the first configuration which can be used to determine said mechanical deformation.

2. The apparatus of claim 1, wherein one of the deformable members is one or more of a stretchable and compressible member configured to allow the proximity of the respective adjacent plasmonic nanoparticles to be increased or decreased between the first and second configurations by the mechanical deformation, respectively.

3. The apparatus of claim 1, wherein one of the deformable members is a flexible member configured to allow the relative orientation of the respective adjacent plasmonic nanoparticles to be varied between the first and second configurations by the mechanical deformation.

4. The apparatus of claim 1, wherein one of the deformable members is configured to undergo expansion between the first and second configurations on absorption of an analyte species from the surrounding environment, and wherein detection of the corresponding change in the resulting plasmon resonance can be used to determine said expansion and hence the presence of the analyte species.

5. The apparatus of claim 1, wherein at least one of the deformable members comprises a substrate on which the adjacent plasmonic nanoparticles are supported.

6. The apparatus of claim 1, wherein the deformable members are interpositioned between the respective adjacent plasmonic nanoparticles.

7. The apparatus of claim 1, wherein at least one pair of adjacent plasmonic nanoparticles are spaced apart from one another by a gap in the first configuration.

8. The apparatus of claim 1, wherein the first second and one or more further plasmonic nanoparticles each have a long axis and a short axis, and wherein the long axis of at least one plasmonic nanoparticle is collinear with the long axis of an adjacent plasmonic nanoparticle in the first configuration.

9. The apparatus of claim 8, wherein the incident electromagnetic radiation is polarized along a predefined polarization axis, and wherein the apparatus is configured such that the long axes of the adjacent plasmonic nanoparticles are aligned substantially parallel to the polarization axis of the incident electromagnetic radiation in the first configuration.

10. The apparatus of claim 1, wherein at least one of the size, shape and material of the first, second and further plasmonic nanoparticles are configured such that that they exhibit their respective plasmon resonances when exposed to one or more of ultraviolet, visible and infrared radiation.

11. The apparatus of claim 1, wherein at least one of the deformable members comprises a reversibly deformable material.

12. The apparatus of claim 1, wherein the mechanical deformation of the deformable members is caused by different stimuli including one or more of thermal expansion and deformation caused by one or more of acceleration, magnetic fields and acoustic pressure.

13. The apparatus of claim 1, wherein at least one of the deformable members comprises one or more of a foam, a cross-linked polymer, a DNA lattice, an elastomer and a block copolymer.

14. The apparatus of claim 1, wherein the first, second and one or more further plasmonic nanoparticles have one or more of the same size, shape and material as one another.

15. The apparatus of claim 1, wherein the first, second and one or more further plasmonic nanoparticles comprise one or more of nanorods, nanowires and nanotubes.

16. The apparatus of claim 1, wherein the first, second and one or more further plasmonic nanoparticles comprise one or more of a noble metal, gold, platinum, silver and aluminum.

17. The apparatus of claim 1, wherein the different types of mechanical deformation comprise tensile, compressive, bending and shearing strain.

18. A method of forming an apparatus, the method comprising:
connecting first, second and one or more further plasmonic nanoparticles to one another by deformable members such that each plasmonic nanoparticle is connected to an adjacent plasmonic nanoparticle using a deformable member, the deformable member connecting one pair of adjacent plasmonic nanoparticles being formed of a different material relative to the deformable member connecting another of adjacent plasmonic nanoparticles such that the deformable member connecting one pair of adjacent plasmonic nanoparticles is configured to monitor a different type of mechanical deformation than the deformable member connecting another pair of adjacent plasmonic nanoparticles, the first, second and further plasmonic nanoparticles each configured to exhibit a respective plasmon resonance when exposed to incident electromagnetic radiation,
wherein, in a first configuration, when adjacent plasmonic nanoparticles are in sufficient proximity to one another their respective plasmon resonances can interact to produce a resulting plasmon resonance, and
wherein mechanical deformation of a deformable member causes a variation in the relative position of the respective adjacent plasmonic nanoparticles to a second configuration to produce a detectable change in the resulting plasmon resonance of the first configuration which can be used to determine said mechanical deformation.

19. A method of using an apparatus,
the apparatus comprising first, second and one or more further plasmonic nanoparticles each configured to exhibit a respective plasmon resonance when exposed to incident electromagnetic radiation, the first, second and one or more further plasmonic nanoparticles arranged such that each plasmonic nanoparticle is connected to an adjacent plasmonic nanoparticle by a deformable member, the deformable member connecting one pair of adjacent plasmonic nanoparticles includes a different material composition to the deformable member connecting another pair of adjacent plasmonic nanoparticles such that each deformable member included in the apparatus is configured to undergo a different type of mechanical deformation, wherein, in a first configuration, the adjacent nanoparticles are in sufficient proximity to one another that their respective plasmon resonances can interact to produce a resulting plasmon resonance, and wherein mechanical deformation of a deformable member causes a variation in the relative position of the respective adjacent plasmonic nanoparticles to a second configuration to produce a detectable change in the resulting plasmon resonance of the first configuration which can be used to determine said mechanical deformation, the method comprising:
determining mechanical deformation of each deformable member based on a detected change in the resulting plasmon resonance of the respective pairs of adjacent plasmonic nanoparticles caused by said mechanical deformation.

20. The method of claim 19, wherein the deformable member connecting one pair of adjacent plasmonic nanoparticles has a material composition comprising an air-gap compressible foam such that the deformable member is configured to undergo a longitudinal tensile strain, and the deformable member connecting another pair of adjacent plasmonic nanoparticles has a material composition comprising graphene oxide foam such that the deformable member is configured to undergo a shearing strain.

* * * * *